United States Patent [19]

Mintz

[11] Patent Number: 5,184,613
[45] Date of Patent: Feb. 9, 1993

[54] THERMAL PACK HEEL WARMING APPARATUS FOR A NEONATE OR INFANT

[75] Inventor: Michael D. Mintz, Edison, N.J.

[73] Assignee: International Technidyne Corporation, Edison, N.J.

[21] Appl. No.: 716,077

[22] Filed: Jun. 17, 1991

[51] Int. Cl.⁵ .............................................. A01F 7/00
[52] U.S. Cl. .................................... 128/402; 128/382
[58] Field of Search .............................. 128/349–403, 128/379, 380, 381, 382; 62/4, 259.3; 126/204, 263

[56] References Cited

U.S. PATENT DOCUMENTS

| | | | |
|---|---|---|---|
| 3,950,158 | 4/1976 | Gossett | 128/403 |
| 3,951,127 | 4/1976 | Watson | 128/403 |
| 4,753,241 | 6/1988 | Branigan et al. | 128/381 |
| 4,780,117 | 10/1988 | Lahey | 62/4 |
| 4,938,222 | 7/1990 | Bier, Jr. | 128/402 |

FOREIGN PATENT DOCUMENTS 2218908 11/1989 United Kingdom ............... 128/403

*Primary Examiner*—Mark Graham
*Attorney, Agent, or Firm*—Arthur L. Plevy

[57] ABSTRACT

A thermal pack has mirror imaged upper and lower sections which are integrally joined by a reduced central section with both the upper and lower sections adapted to be secured about a corresponding limb of a user with the reduced area central portion serving as a hinge to surround the joint of the user when accommodating the thermal pack. The thermal pack is further characterized in that the entire major surface of the thermal pack is manifested by a plurality of compartments giving the thermal pack a quilted-like appearance. Each of the compartments may communicate with one another via formed passageways within the compartments containing a chemical fluid substance which is adapted to release or absorb heat when subjected to activation.

16 Claims, 3 Drawing Sheets

THERMAL PACK HEEL WARMING APPARATUS FOR A NEONATE OR INFANT

BACKGROUND OF THE INVENTION

This invention relates to thermal pack devices, in general, and more particularly to a thermal pack utilized for warming the heel of an infant prior to obtaining a blood sample from the infant.

The field of thermal packs as those which produce heat or cold upon selective operation is replete with a large number of patents. Essentially, there are numerous types of thermal packs which are readily available according to such prior art techniques. Such packs exist in the marketplace and are sold by many companies. The typical thermal pack employs a sealed rectangular or other shaped package containing selected chemical ingredients which when finally intermixed together, provide either a refrigerated pack or a heated pack. As indicated, there are numerous examples in the prior art showing such techniques. References is made, for example, to U.S. Pat. No. 4,057,047 issued on Nov. 8, 1977 to R. L. Gossett and entitled MAGNESIUM SULFATE ANHYDROUS HOT PACK HAVING AN INNER BAG PROVIDED WITH A PERFORATED SEAL. See also U.S. Pat. No. 4,856,651 entitled CHEMICAL THERMAL PACK AND METHOD OF MAKING THE SAME to S. E. Francis, Jr. issued on Aug. 15, 1989. See also U.S. Pat. No. 4,580,547 entitled FLEXIBLE HEAT PACK CONTAINING SUPERCOOLED SALT SOLUTION by Kapralis et al. issued on Apr. 8, 1986.

Each of these thermal packs incorporate trigger mechanisms whereby when triggered, a heat or cooling reaction will take place. For such operations one can refer to other references such as U.S. Pat. No. 2,925,719 to A. A. Robbins wherein a refrigerating pack is provided containing a refrigerating chemical such as ammonium nitrate for reaction with water when an inner envelope is broken. The concept of enveloping one package within the other is well known in the prior art. See, for example, U.S. Pat. No. 2,907,173 issued to A. A. Robbins as well as U.S. Pat. No. 4,057,047 which shows a thermal reaction package utilized as a thermal pack whereby one compartment contains a quantity of urea while the other compartment is intended to be filled with water to create an endothermic or cooling reaction when mixed with the urea. As indicated, there is a plethora of patents in the prior art which teach the use of all types of chemicals which can be employed to operate in a thermal heated or refrigerated pack and which require the activation of a trigger to actuate the reaction to produce the effect. Reference is again made to the above-noted patent, U.S. Pat. No. 4,580,547 where a trigger is located in a container and when the trigger is deformed, chemical crystallization is initiated to produce heat. The trigger may comprise a thin, bendable metallic strip which can be activated when the trigger is in any position. The trigger which is located in the container is adapted to be deformed to initiate exothermic crystallization of a salt which is in a solution. The number of salts which store heat as the heat of fusion and which release heat upon crystallization are numerous. See, for example, U.S. Pat. No. 3,536,058 issued on Oct. 16, 1970 to Hearst et al. and entitled CHEMICAL HEAT BARRIER FOR WETSUITS. This patent describes many such salts, typical examples being sodium sulfate decahydrate, disodium phosphate dodecahydrate, as well as lithium nitrate trihydrate. Furthermore, it is well known to utilize mixtures of hydrated salts in supercooled liquid form to produce controlled eutectic temperatures of crystallization. There are virtually numerous salts which when activated by a trigger such as a suitable metal or other substance, will crystalize to produce heat. Basically such salts and materials may be referred to as temperature altering chemicals.

Thus, as one will appreciate, the above-noted patents and a host of other patents as well, describe various packages for applying heat or cold to applicable parts or areas of the body when activated or otherwise employed to keep a person or user warm under adverse ambient conditions. In this particular application, there is disclosed a thermal pack of a unique configuration which is intended to be used on an infant and to generate heat at a controlled temperature which allows the heel of the infant and its surrounding tissue as, for example, the leg and foot, to be elevated to a temperature of about 42° C. In this manner the thermal pack will enable the blood vessels to dilate and thereafter a medical practitioner can puncture the heel of the infant to obtain a blood sample with a better blood flow because of the heated expanded blood vessels. Also, in the event that the sample is taken for the purpose of doing a blood gas analysis, it is necessary that the infant's foot be pre-warmed and the vessels be pre-warmed before the sample is taken. Generally speaking, it is required by legislation that every neonate have blood tests performed. Thus, every infant that is born in the United States has a blood sample drawn from a puncture usually made in the heel of the infant. These procedures utilize an instrument for making such incisions such as the TENDERFOOT instrument marketed and sold by the assignee herein.

Thus, it is an intent of the present application to provide a thermal pack which is particularly adapted for the above-noted use.

It is a further objective to provide a thermal pack of a unique configuration which can be triggered when use is desired and upon triggering, produces a phase transition from a supercooled liquid to a crystalline form and to emit a controlled heat.

As will be described, the thermal pack according to this invention is extremely easy to utilize and it is symmetrical so that it can be used by right or left handed persons with extreme ease and simplicity. The thermal pack is of a unique configuration to enable the heating of the heel of an infant to accommodate the required blood sampling.

SUMMARY OF THE INVENTION

A thermal pack comprising a flexible fluid containing pouch having an hour glass-like configuration with a reduced area central portion bounded by an upper portion having left and right extending flaps symmetrically disposed about said central portion, and a lower portion having left and right extending flaps of the same configuration as those of said upper portion and symmetrically disposed about said central portion, said pouch divided into a series of fluid containing compartments for accommodating a heat producing chemical solution and providing to said pouch a quilt-like appearance, and means associated with said upper and lower portions to enable said flaps to be secured to one another to cause said pouch to assume a cylindrical configuration of variable diameters according to the dimensions of said upper and lower portions and said flaps.

DETAILED DESCRIPTION OF THE FIGURES

Figure 1:
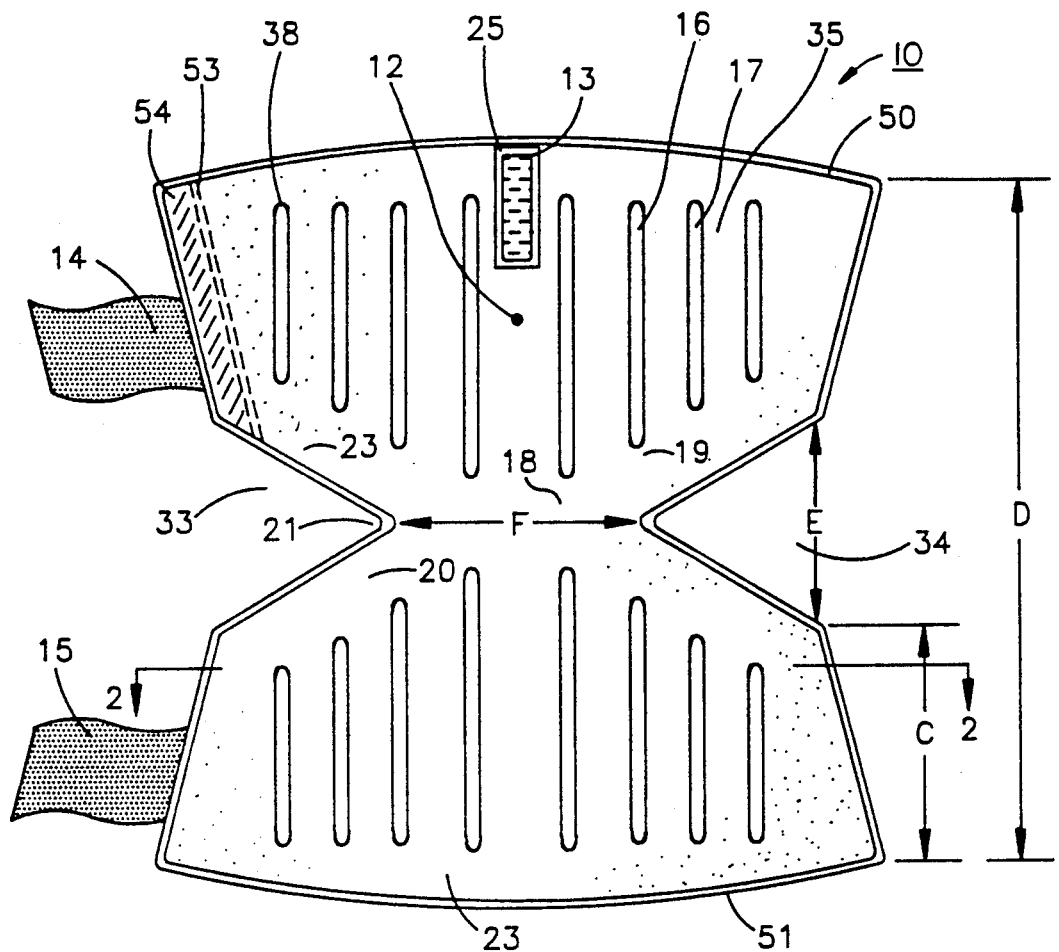
FIG. 1 is a top view of a thermal pack according to this invention.
Figure 2:
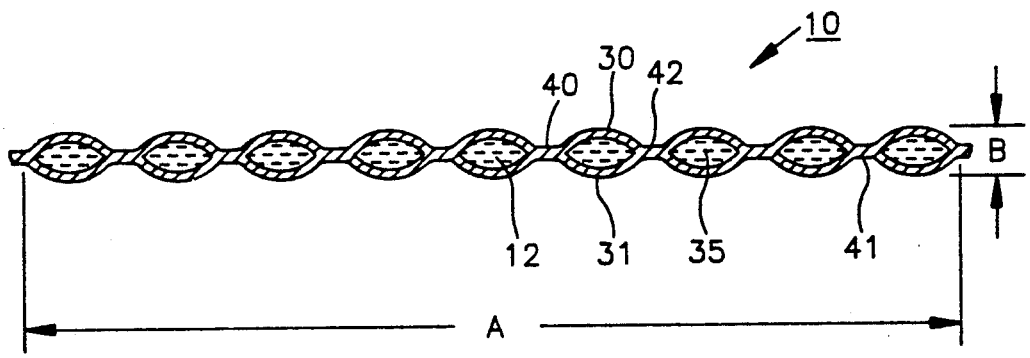
FIG. 2 is a cross-sectional view taken through line 2—2 of FIG. 1.
Figure 5:
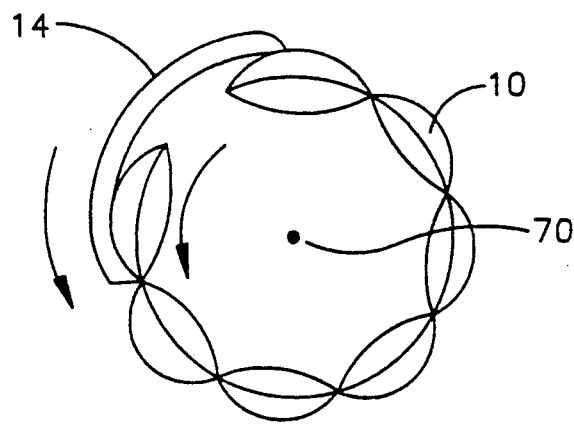
FIG. 5 is a front view depicting the thermal pack in an operative position.

Referring to FIG. 1 there is shown a top view thermal pack member 10 according to this invention. The thermal pack member 10 essentially consists of a folded single sealed sheet or two sealed sheets of plastic which are more particularly shown in FIG. 2. There is a top sheet 30 and a bottom sheet 31, each fabricated from a suitable and typical plastic such as polyvinylchloride (PVC), polyethylene, axial nylon or some other flexible transparent commercial plastic, numerous examples of which exist in the market. It is preferable that the plastic be of the type that can be sealed by conventional techniques such as radio frequency (RF) heat sealing, impulse heat sealing, and so on. Essentially each of the plastic sheets as 30 and 31 are relatively thin. The entire thermal pack 10 is basically symmetrical in shape and has a substantially reduced area central portion 21. The thermal pack 10 represents a preferred embodiment of the invention and is basically symmetrical in shape. The reduced central section 21 is bounded by left and right side triangular shaped apertures as 33 and 34. The central portion 21 serves as a living hinge to enable the thermal pack to comfortably encircle a portion of an infant's leg as well as the heel and foot area with the hinge provided by the reduced central area 21 acting as a transition area to cover the heel and to enable the surrounded ankle to move comfortably. The member 10 has a large surface area as seen in FIG. and a small cross-sectional area as seen in FIG. 2. It is basically a planar member and is sheet-like in nature so it can be folded easily and conveniently mainly due to the compartmental or quilted configuration, but also due to the relative thickness of the thermal pack 10. As seen in FIG. 1, the member basically is symmetrically shaped and assumes an hour glass or Figure "8" type of configuration with the sections above and below the center hinge section 21 being symmetrical. The member is characterized in having a plurality of parallel seams or ribs as 16 and 17 perpendicular to top and bottom edges of the member, each of which separates the member into a plurality of individual fluid-containing compartments such as compartment 35. The compartments and the sealed boundaries therebetween give the member 10 a quilt-like appearance. As one can see from FIG. 2, the surfaces of the thermal pack 10 appear quilted due to the convex projections manifesting the top and bottom of each compartment as 35. In FIG. 5 it can be seen that the member allows air pockets to form above the seams when the member is encircled around a substantially cylindrical shape on either side of the central area. The compartments are fabricated in the plastic by a typical heat sealing technique which essentially operates to seal sheets 30 and 31 at areas as 40, 41 and 42 as shown, for example, in FIG. 2. The heat sealing of plastics is extremely well known in the prior art and there are various well known techniques for thermally sealing one plastic sheet to another. Also shown in the heat sealed areas are openings or passageways such as 18, 19, 20, 23, and so on, to allow the fluid or material 12 contained within the hollow confines of the quilted-like member 10 to circulate freely throughout the member. While various passageways are shown, such as 20 and 23, it is of course understood that the location or shape of such passageways can vary in any desired manner. In any event, the thermal pack 10 has two extending tabs 14 and 15 located as shown on the left side and which tabs are suitably coated with a reusable adhesive. The tabs enable one to fold or locate the member 10 about the limb of a user or other area. As indicated, each of the compartments as, for example, compartment 35 (FIG. 2) contains a suitable fluid, which fluid contains a chemical formulation which when activated or triggered, produces or absorbs heat. For example, the fluid 12 contained within the flexible thermal pack 10 may include sodium acetate and sodium thiosulfate both in hydrated form. The supercooled solution containing these salts may also contain surplus water or other substances to stabilize the supercooled state of the solution. Further, in order to maintain pliability and softness, materials such as soaps, glycerine, fatty acids or sand are also included so that the crystal that is eventually formed by the heat of crystallization is relatively small and therefore the package or thermal pack remains extremely pliable. As seen, there is a pouch 13 which is heat sealed to the peripheral edge of the two plastic sheets and which contains a suitable trigger mechanism 25 which, for example, can be a crystalline particulate or some other well known trigger mechanism as described in the prior art. While it is indicated that the device is made of two sheets of plastic, it is also understood that the device could be made of a single sheet of plastic and folded at the top edge 50 or at the bottom edge 51 and then sealed about the periphery as can be understood from the configuration shown in FIG. 1. In this manner the entire plastic member 10 consisting of the above-noted sheets can be fabricated by means of a die cut or other conventional plastic fabrication technique.

Figure 3:
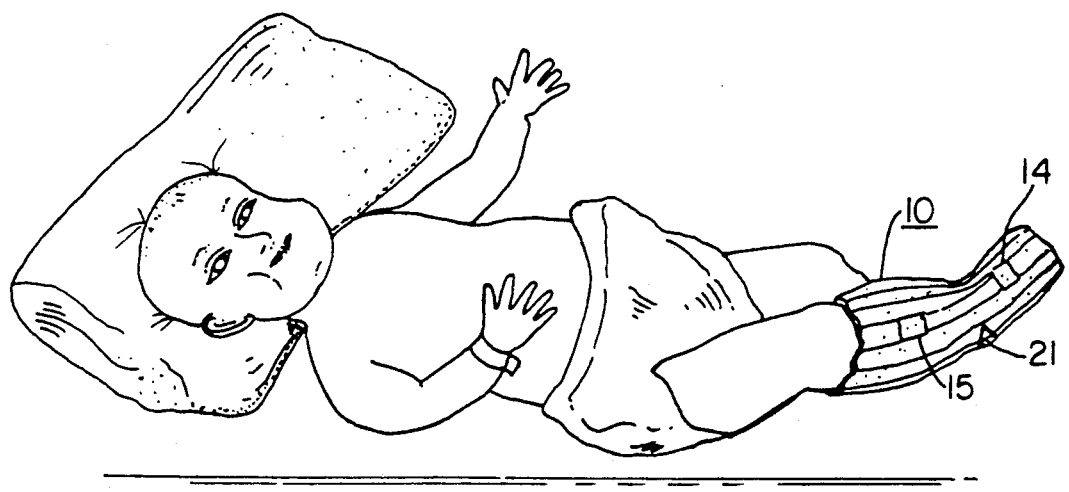
FIG. 3 is a perspective plan view showing a thermal pack being applied to the foot of an infant.
Figure 4:
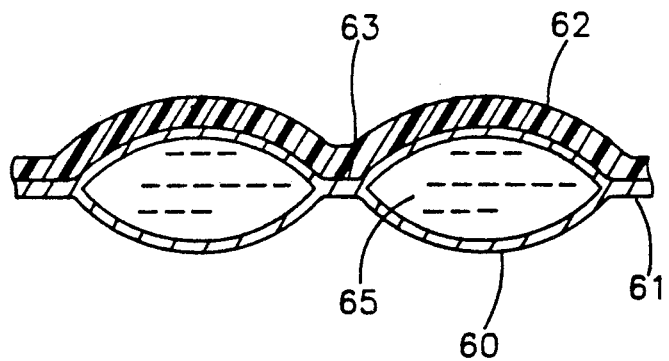
FIG. 4 is a partial cross-sectional view of an alternate embodiment of the invention.

Referring to FIG. 3 there is shown the thermal pack 10 accommodated about the heel and adjoining leg and foot portions of an infant from whom blood is to be taken as above indicated. The entire unit 10 as shown in FIG. 1 is extremely pliable as it is made out of a very thin plastic sheet and has the supercooled, liquid hydrated salt solution contained within the compartments of the quilt-like plastic member. The member is relatively thin and perhaps the largest section would be ½ inch thick. Essentially the user places the reduced central cross-section 21 about the heel portion of the leg of the infant. In this manner the flap, for example, 14 is together with its associated mirror image flap and is wrapped around the foot of the infant. The thermal pack 10 is shown encircling the arch of the infant's foot or the entire foot as shown in FIG. 3, while the remaining section which includes flap 15 is then emplaced about the portion of the infant's leg above the ankle as shown in FIG. 3. The adhesive tab members 14 and 15 enable one to firmly secure the entire thermal package 10 about the infant's foot and leg as shown. The plastic pouch 13 containing the activator or trigger 25 may include, for example, a suitable colorant such as a vegetable dye, and so on. In this manner the operator bursts the plastic pouch 13 which is essentially a bubble-like structure and activates the reaction before emplacing the device about the leg of an infant. The chemical 25 contained within the pouch 13 is readily viewable, and the pouch 13 is easily available. Again referring to FIG. there is shown a dashed line boundary 53 drawn on the left hand side of the top flap of the thermal pack 10 adjacent the tab 14. The boundary 53 forms a truly partitioned compartment in which a chemical or other activator material 54 is located and is isolated from the liquid 12 by the wall or compartment boundary 53. The compartment formed by the partition 53 may be substituted for the pouch 13, whereby activator materials 54 and 25 are identical and the pouch 13 and compartment formed by partition 53 serve identical functions. In order to discharge the activator one grasps the area, exerts a force on the activator fluid 54 to thus rupture the seal formed by the wall 53 to enable the activator to be dispersed into the fluid creating an exothermic or endothermic reaction depending upon the chemicals employed. As one will understand, because of the narrowed central section of the thermal pack 10, it can be bent and placed comfortably over the heel and leg of the infant and due to its pliability and flexibility can easily be accommodated to fit typical joints. While the thermal pack has great utility in association with thermal packs used in conjunction with blood heating of neonates, it has applicability for use with individuals of all sizes, as adults, children, and so on, both as a heat or cold pack. Typical dimensions for use with neonates are given with reference to FIGS. 1 and 2. Dimension A which is the largest width of the pack is between 5.5 to 6.0 inches. Dimension B which is the maximum thickness is between ¼ to ½ inch, depending upon the amount of liquid to be accommodated, ⅜ inch is preferable. Dimension C which is the length of a flap is about 2 inches. Dimension D is the length of the pack 10 and is about 5.5 to 6.0 inches. Dimension E is 1-2 inches. Dimension F is between 2-3 inches, and so on. The above dimensions are only by way of example and any other dimensions can be employed. The peripheral edges or sides of the pack 10 can be straight and will attain a slightly curved condition as shown when the pack 10 has been filled with the reactant chemicals as described. The activating element can consist of many things such as a metal trigger or certain chemicals such as sodium borite which can be suspended in a peanut oil or other similar type of chemical which would enable one to trigger the reaction in the supercooled liquid. As one will understand, the hourglass shape of this particular thermal pack is extremely important for the application. This enables the thermal pack to form the dual function of heating the infant's heel area while further heating the blood vessels which extend into the heel area from the leg and foot of the infant. The symmetrical nature of the pack enables the formation of the hinge area 21 while the quilted nature of the pack enables one to bend the pack in an infinite number of positions to thereby accommodate flexing of the ankle. The entire unit is totally symmetrical and thereby can be utilized with ease by either left handed or right handed individuals with a minimum of effort. It will be understood that the upper and lower right or left flaps in pairs as shown in FIG. 1 contribute to the ease of placement of the thermal pack 10 about a body joint. However, one flap of each pair of flaps may be eliminated with the remaining flap serving as the wrap around and having the adhesive tab. While the unit is fabricated from a single or two plastic sheets as above indicated, it can also be fabricated from composite, flexible materials. For example, referring to FIG. 4 there is shown a partial cross-section of a typical alternate construction of materials which can formulate the configurations shown in FIG. 1. Shown in FIG. 4 is a partial cross-sectional view of a quilted configuration which essentially consists of a sheet of plastic 60 which can be the type of plastic indicated above which is heat sealed to another sheet of plastic 61 which has located thereon a layer of insulating material 62 which may be secured thereto by means of a heat seal 63 or by an epoxy or other type of glue. Again, the partial cross-sectional view makes up the member as shown in FIG. 1 with a suitable liquid 65 retained within the plurality of compartments formed in the quilted member as shown in FIG. 1. As seen, the insulator layer 62 will serve to retain heat to thereby enable the device to be used to sooth muscle aches, and so on. The pack 10 can be used for adults and utilized on other parts or portions of the human anatomy. The layer 62 is an insulating layer and thereby would be emplaced away from the skin of the user with the layer 60 directly contacting the skin. In this manner heat or cold, depending on a chemical composition 65, would be available via the thermal pack for longer periods of time. Apart from the symmetrical shape of the structure shown in FIG. 1, it is also noted that the quilted effect of the device is extremely important to prevent the opposing walls of the device such as defined by sheets 30 and 31 of FIG. 2 from separating too much while creating compartments or cells which have limited areas of communication. Thus the heat seals which are formed between the compartments terminate to form an upper communication passageway as 38 as well as a bottom communication passageway between the compartments. Passageways as 20 and 23 and 18 and 19 can also be formed to enable the fluid contained within the compartments to flow between each of the cells or compartments to therefore maintain a relatively uniform pressure when the device is emplaced upon the limb or other area of a user and to permit the phase-change process to propagate between each of the cells or compartments.

As is also understood, there are many different chemicals which can be employed with the pouch 13 and serve to operate as chemical 25. The pouch 13 is preferably heat sealed between the two plastic sheets 30 and 31 and is fixed in position. It is also understood that the pouch can be free-floating within the pack 10, due to the fact that a vegetable dye or other coloring can be added for visibility. In any event, it is preferable to secure the pouch to the peripheral edges of the thermal pack 10 to enable easy utilization of the same, or alternatively to replace the pouch 13 with the compartment formed by the partition 53.

Figure 6:
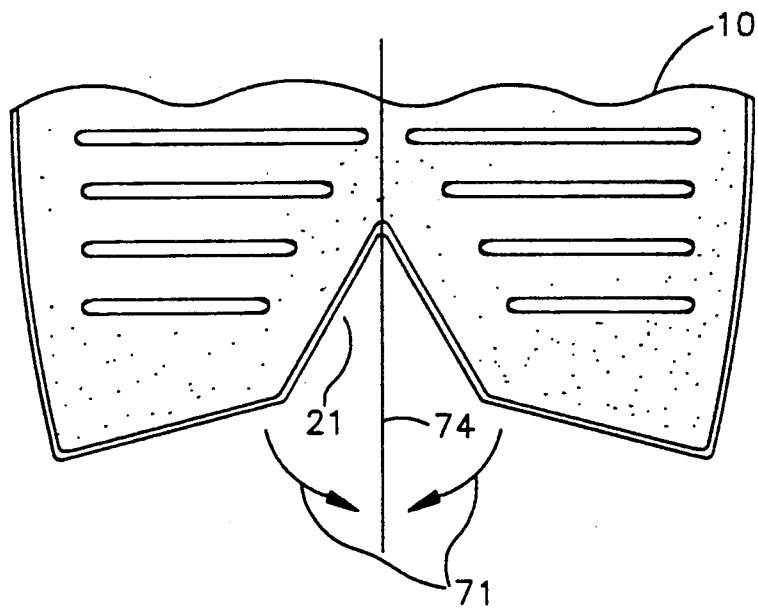
FIG. 6 is a side view of the thermal pack in an operative position.

Thus the above-noted device, based on its shape, is adaptable to conform particularly to a body joint such as an elbow, a knee, or heel, and has at least two sections which are essentially of the same dimensions so it does not matter how the device is applied or whether the person utilizing the device is a left handed or right handed perso. The pack 10 is adjustable and completely pliable. In FIG. 5 the arrows indicate the adjustability features and how the tabs as 14 can be moved to change the diameter of the devices with respect to the center 70. The side view is shown in FIG. 6 to show how the device is adjusted about the center line 74 in the direction of arrow 71. Thus the reduced middle sectional area 21 functions as a hinge that wraps around the particular joint to which the device is to be secured. For example, assume that the thermal pack 10 is to be utilized in conjunction with an elbow. In this manner the reduced area central portion 21 would be positioned at the joint of the elbow with the top area associated with the flap 14 positioned about the biceps area of the patient and with the bottom portion associated with flap 15 positioned about the forearm of the patient, near the elbow. As one can ascertain, the strips 14 and 15 would be secured to the opposite ends as the entire thermal pack 10 is enwrapped about the limb or the elbow of the patient as described. In this manner the pressure which is developed by the pack 10 at the elbow would be optimumly maintained to the extremity of the joint due to the fact that the member is secured at the top and bottom portions by means of the tape or VELCRO tabs 14 and 15. While the sections are shown as symmetrical, it is of course understood that they need not be absolutely symmetrical but should be relatively close in size to enable the entire unit to be wrapped front or back as above indicated.

Another advantage of the above-noted apparatus is that due to its flexibility and construction and basically due to the series of compartments in the quilted-like configuration, the device does not act as a tourniquet or impede the flow of blood. This is extremely important as many of the devices of the prior art could, in fact, if improperly applied, act as a tourniquet and therefore substantially affect circulation. This device is such that the hinge portion formed about the reduced central section is wrapped about the joint and it is extremely difficult in any manner to encircle the portions of the limb above and below the joint to substantially affect blood flow. While the unit is shown in FIG. as having a plurality of different compartments each of which contains fluid, it is of course understood that certain of the areas can remain flat and hence no fluid be included and therefore the device can be wrapped selectively around portions of the anatomy instead of an entire joint, and so on.

Because the device is relatively simple, extremely flexible and conformal, it can be totally sterilized by conventional techniques. For example, one can utilize conventional sterilization provided that the temperature is not raised above the deformation temperature of the plastic, and so on.

As one can ascertain from the above, it is absolutely apparent that many modifications and variations apart from those already discussed are possible.

There are many different types of plastics which can be used as well as many different heat sealing techniques for forming the pack. The pack can be made of multiple sheets of plastic of a composite nature including insulators or can be fabricated from single sheets. The plastic may be die cut or formed in any other manner. It is therefore to be understood that within the scope of the appended claims, the invention may be practiced otherwise than as specifically described.

I claim:
1. A thermal pack comprising:
a first and second wall, joined along a common periphery in a fluid impermeable manner, forming a flexible fluid containing pouch, said pouch being substantially symmetrically formed on either side of a narrowed central region forming a substantially hour-glass shaped configuration, said first and second walls being joined along a plurality of substantially parallel seams in a fluid impervious manner, dividing said pouch into a series of fluid containing compartments, said seams not extending to the edges of said pouch, allowing said fluid containing compartments to interconnect along the peripheral regions of said pouch; and
a securing means associated with said pouch on both sides of said central region enabling said pouch, on either side of said central region to assume a substantially cylindrical configuration of a variable diameter.

2. The thermal pack of claim 1, wherein said pouch contains at least one chemical compound capable of undergoing an endothermic reaction when actuated or at least one chemical compound capable of undergoing an exothermic reaction when actuated.

3. The thermal pack of claim 2, wherein said thermal pack further includes a rupturable packet, contained within said pouch, said rupturable packet containing at least one activating agent for activating an endothermic reaction in said endothermic reaction chemical compound or at least one activating agent for activating an exothermic reaction in said exothermic reaction chemical compound.

4. The thermal pack of claim 3, wherein said chemical compound includes a solution with an activatable salt which selectively undergoes a phase transition from a supercooled liquid to a crystalline form, providing heat at a predetermined temperature, when said exothermic reaction chemical compound reacts with said exothermic reaction activating agent.

5. The thermal pack of claim 4, wherein said activatable salt includes sodium acetate.

6. The thermal pack of claim 4, wherein said predetermination temperature is approximately 42° C.

7. The thermal pack of claim 3, wherein said first and second walls are fabricated from a substantially translucent material.

8. The thermal pack of claim 7, wherein said activating agent held within said rupturable pack is colored to contrast with the color of said chemical compound held in said pouch.

9. The thermal pack of claim 8, wherein said rupturable packet is positioned in the peripheral region of said pouch wherein said fluid containing compartments interconnect.

10. The thermal pack of claim 1 where said seams do not extend into said central region allowing said fluid containing compartments to interconnect within said central region.

11. The thermal pack of claim 1, wherein said pouch has a top edge and a bottom edge such that said substantially hour-glass shaped configuration is formed therebetween and said narrowed central region is centrally positioned between said top edge and said bottom edge, and wherein said seams defining said fluid containing compartments, lay in a substantially perpendicular orientation to said top and bottom edge in said pouch.

12. The thermal pack of claim 1, wherein said first and second walls comprising said fluid containing compartments are substantially convex in between said parallel seams, the convex shape of said first and second walls allowing air pockets to form above said seams as said pouch is encircled around a substantially cylindrical shape on either side of said central region.

13. The thermal pack of claim 11, wherein said narrowed central region is approximately one half as wide as said top and bottom edge.

14. The thermal pack of claim 13, wherein the distance between said top edge and said bottom edge is substantially equal to length of said top edge and said bottom edge.

15. The thermal pack of claim 10, wherein said pouch, on either side of said narrowed central region has a maximum width of between 5.5 inches and 6.0 inches thereby being wide enough to be encircled around the foot of a neonate.

16. The thermal pack of claim 14, wherein said top edge and said bottom edge are between 5.5 inches and 6.0 inches in length.

* * * * *